United States Patent [19]

Schmidt

[11] 4,358,270

[45] Nov. 9, 1982

[54] DENTAL INSTRUMENT RETRACTION ACTIVATOR

[75] Inventor: Manfred Schmidt, Karlsruhe, Fed. Rep. of Germany

[73] Assignee: Sybron Corporation, Rochester, N.Y.

[21] Appl. No.: 150,058

[22] Filed: May 15, 1980

[30] Foreign Application Priority Data

Apr. 10, 1980 [DE] Fed. Rep. of Germany ....... 3073883

[51] Int. Cl.³ ............................................... A61C 1/14
[52] U.S. Cl. ......................................... 433/78; 433/27
[58] Field of Search ...................... 433/78, 77, 28, 27, 433/98, 101; 242/54 R; 307/39; 200/331, 61.15; 324/206, 208

[56] References Cited

U.S. PATENT DOCUMENTS

| | | | |
|---|---|---|---|
| 3,264,629 | 8/1966 | LeBus, Sr. | 324/206 |
| 3,266,745 | 8/1966 | Benson | 200/61.15 |
| 4,012,002 | 3/1977 | McDonald et al. | 242/54 R |
| 4,106,005 | 8/1978 | Asakawa | 324/208 |
| 4,114,273 | 9/1978 | McGaha | 433/27 |
| 4,140,971 | 2/1979 | Blincoe | 324/208 |
| 4,161,659 | 7/1979 | Jacob | 307/39 |

FOREIGN PATENT DOCUMENTS 2705209 8/1978 Fed. Rep. of Germany ........ 433/78

Primary Examiner—Paul J. Hirsch
Assistant Examiner—John J. Wilson
Attorney, Agent, or Firm—Theodore B. Roessel; J. Stephen Yeo; Robert J. Bird

[57] ABSTRACT

One or more dental instruments are connected by flexible supply lines to a dental unit. A retractor is arranged to pull an extended instrument back to the unit upon being triggered. The dental instrument carries a magnet. A magnetic sensor is located near the retractor. When the instrument is passed near to sensor a signal activates the retractor which pulls in the instrument.

1 Claim, 2 Drawing Figures

DENTAL INSTRUMENT RETRACTION ACTIVATOR

BACKGROUND OF THE INVENTION

This invention pertains to dental instruments and is more particularly concerned with apparatus for retracting dental instruments.

Dental instruments such as syringes, drills, aspirators, scalers and electrosugery probes are often stored in a console or dental unit instrument delivery. The instruments are connected to supplies by means of flexible supply lines. A number of retraction schemes are known which include mechanisms associated with the dental unit.

At least one scheme exerts a small but constant pull upon each dental instrument. This force is easily countered by the dentist when he is using the instrument, but upon release of the instrument, it is retracted to the dental unit. In other arrangements there is no retraction force upon the line while the instrument is in use. When the instrument is returned to the dental unit, the dentist must either pull the hose to release a locking mechanism or to touch a switch or other activator on the dental unit. Both arrangements cause the dentist to perform a superfluous movement.

It is the object of this invention to provide a retraction activator for causing retraction of an extended dental instrument into storage in a dental unit when the dental instrument is simply passed near the dental unit.

SUMMARY OF THE INVENTION

One or more dental instruments are connected by flexible supply lines to a dental unit. A retractor is arranged to pull an extended intrument back to the unit upon being triggered. The dental instrument carries a magnet. A magnetic sensor is located near the retractor. When the instrument is passed near to sensor a signal activates the retractor which pulls in the instrument.

DESCRIPTION OF THE PREFERRED EMBODIMENT

Figure 1:
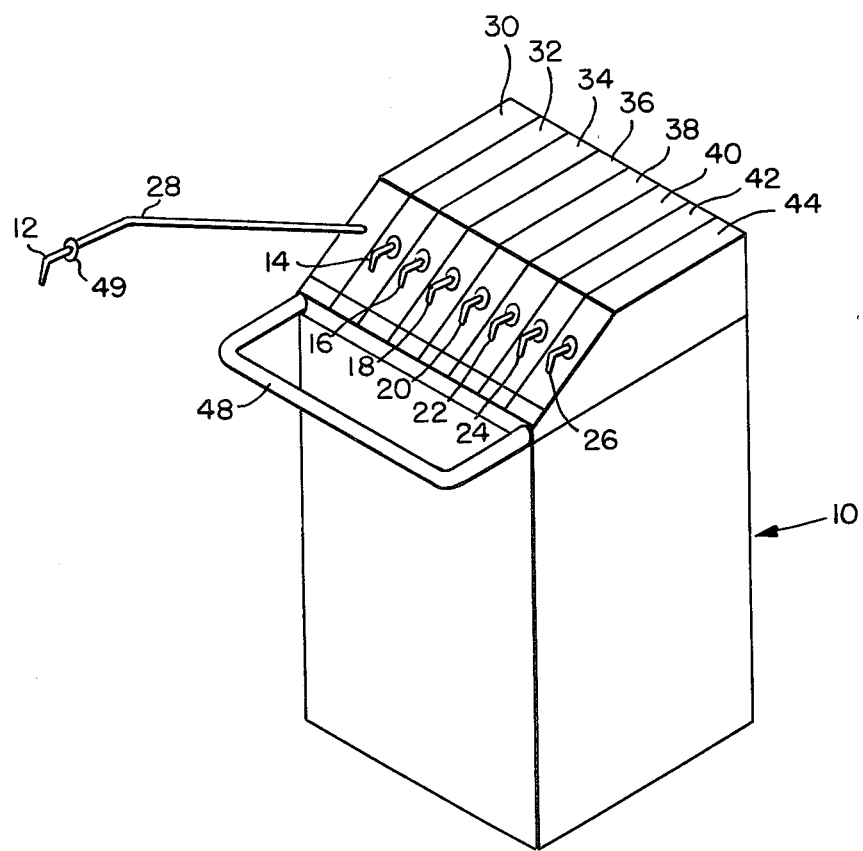
FIG. 1 is a schematic representation of a dental unit having a dental instrument retraction activator according to the invention.

Referring to FIG. 1, a dental unit which stores a plurality of dental instruments 12-26. The instruments are connected by flexible supply lines 28 to supplies within the dental unit 10. Each dental instrument is provided with a individual retraction mechanism 30-44 that, upon activation by an electrical signal pulls the line of the extended instrument back into the dental unit. A suitable retraction mechanism is described in a copending U.S. patent application Ser. No. 240,486 filed Mar. 4, 1981. As a feature of the invention, a magnetic sensor 46 is arranged at the front of the dental unit, close to the path the instrument would take if it were manually returned to the dental unit. The sensor 46 may be located with a handle of the unit. In one form the sensor is a coil and is wound about an iron or ferret core rod which extends across the width of the unit. When a magnetic field is moved past the sensing coil or the core, there is, in accordance with Faraday's law, an electrical pulse generated within the coil.

As another feature of the invention, each instrument associated with the dental unit is provided with a magnetic field from permanent magnets. If an instrument has a DC motor with permanent magnets no additional magnets are necessary. For other instruments where no magnetic field normally found, the magnetic field may be supplied by a permanent magnet 50 carried by the instrument, preferably at the coupling with the supply line. A dentist using apparatus embodying the invention would simply pass the instrument near the dental unit when he desires it to be retracted. The magnet causes an electric trigger signal to be generated in the magnetic sensor which is amplified and activates the retraction mechanism of the extended unit.

Figure 2:
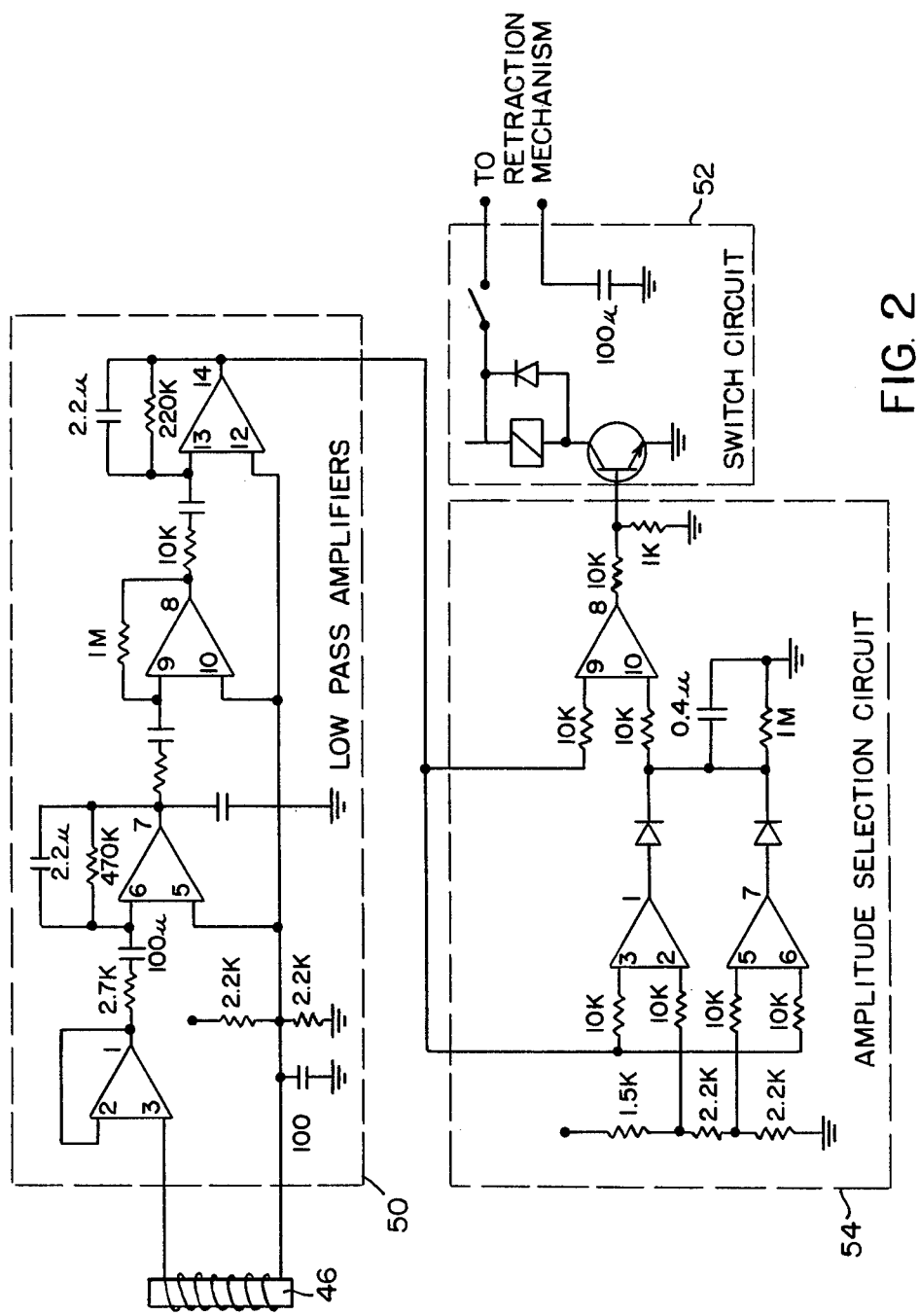
FIG. 2 is a schematic drawing of circuitry suitable for use in the arrangement of FIG. 1.

In keeping with this invention, the trigger signal is amplified by low noise sensitive low pass amplifiers 50 seen in FIG. 2. The amplified trigger signal then triggers a switch circuit 52 such as a controlled rectifier, relay or logic circuitry.

The switch circuit 52, when triggered, energizes the retraction mechanism which pulls the line of the instrument back into the dental unit. Preferably, the switch circuit will operate only when the amplified signal is above a threshold voltage. For this reason, an amplitude selection circuit 54 such as a threshold or window discriminator may be in series between amplifier 50 and switch circuit 52.

In keeping with the invention, a "clear" signal may be supplied by the circuit to "clear" other circuitry used in the unit 10.

I claim:

1. A dental instrument retraction activator comprised of:
    at least one dental instrument characterized by having a magnetic field;
    a retraction mechanism which is activated by an electrical signal;
    a supply line attached to the dental instrument and running to the retraction mechanism;
    a magnetic sensor is arranged in proximity to the retraction mechanism which generates an electrical signal in response to a moving magnetic field if the dental instrument is passed by the sensor;
    a low pass filter and an amplitude selective circuit in series with said sensor for providing a low noise amplitude electric signal; and
    means for providing a retractor activating electrical signal in response to the amplified electric signal.

* * * * *